United States Patent [19]

Mackin

[11] Patent Number: 4,961,738
[45] Date of Patent: * Oct. 9, 1990

[54] ANGIOPLASTY CATHETER WITH ILLUMINATION AND VISUALIZATION WITHIN ANGIOPLASTY BALLOON

[76] Inventor: Robert A. Mackin, 329 W. Granada Ave., Phoenix, Ariz. 85003

[*] Notice: The portion of the term of this patent subsequent to Nov. 15, 2005 has been disclaimed.

[21] Appl. No.: 127,923

[22] Filed: Dec. 2, 1987

Related U.S. Application Data

[63] Continuation-in-part of Ser. No. 8,276, Jan. 28, 1987, Pat. No. 4,784,133.

[51] Int. Cl.$^5$ ............................................. A61B 17/36
[52] U.S. Cl. ......................................... 606/15; 128/6
[58] Field of Search ........................................ 128/4–8, 128/303.1, 395–398; 604/96–98, 103; 606/13–16

[56] References Cited

U.S. PATENT DOCUMENTS

| | | | |
|---|---|---|---|
| 4,224,929 | 9/1980 | Furihata | 128/5 |
| 4,418,689 | 12/1983 | Kanazawa | 128/6 |
| 4,445,892 | 5/1984 | Hussein et al. | 604/101 |
| 4,448,188 | 5/1984 | Loeb | 128/395 |
| 4,470,407 | 9/1984 | Hussein | 128/398 |
| 4,545,390 | 10/1985 | Leary | 604/96 |
| 4,624,243 | 11/1986 | Lowery et al. | 128/6 |
| 4,672,961 | 1/1987 | Davies | 128/303.1 |
| 4,784,133 | 11/1988 | Mackin | 128/303.1 |

FOREIGN PATENT DOCUMENTS

| | | | |
|---|---|---|---|
| 0121215 | 10/1984 | European Pat. Off. | |
| 0178464 | 4/1986 | European Pat. Off. | 128/303.1 |
| 2847633 | 2/1978 | Fed. Rep. of Germany | |
| 2163055 | 2/1986 | United Kingdom | |

*Primary Examiner*—Max Hindenburg
*Attorney, Agent, or Firm*—Cahill, Sutton & Thomas

[57] ABSTRACT

An angioplasty catheter includes a light source and eyepiece connected by a cable to a proximal portion of a stiff inner catheter of the angioplasty catheter. A plurality of optical fibers carrying light from the light source are attached to or embedded in the stiff inner catheter and terminate just inside an inflatable transparent balloon of the angioplasty catheter to illuminate the interior of the balloon and the walls of an artery, and plaque or other obstruction in the artery. A plurality of optical fibers with distal ends in the proximal portion of the balloon are embedded in or attached to the stiff inner catheter and have proximal ends connected to the eyepiece to enable a physician to view the walls of the artery and the plaque or obstruction before, during, and after an angioplasty procedure.

13 Claims, 4 Drawing Sheets

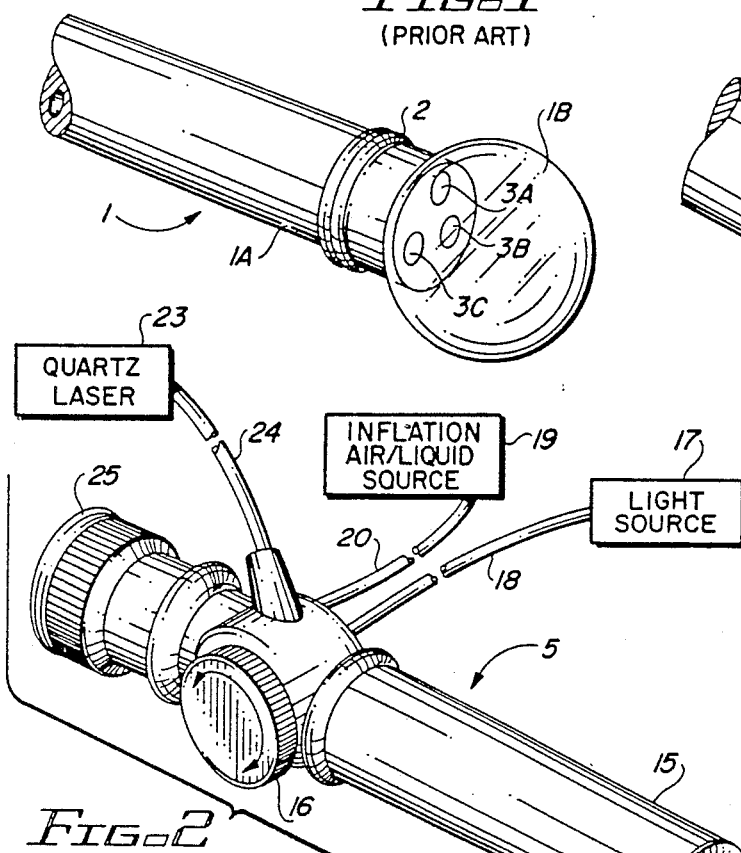
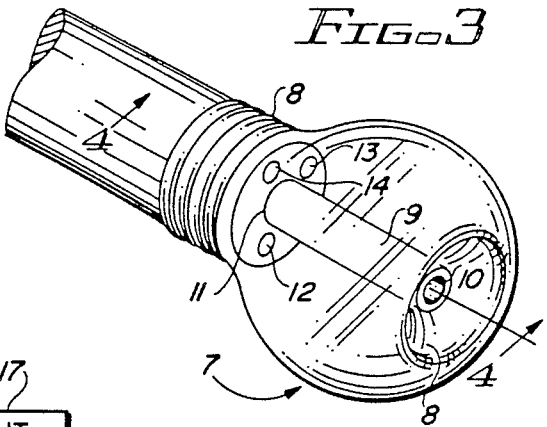
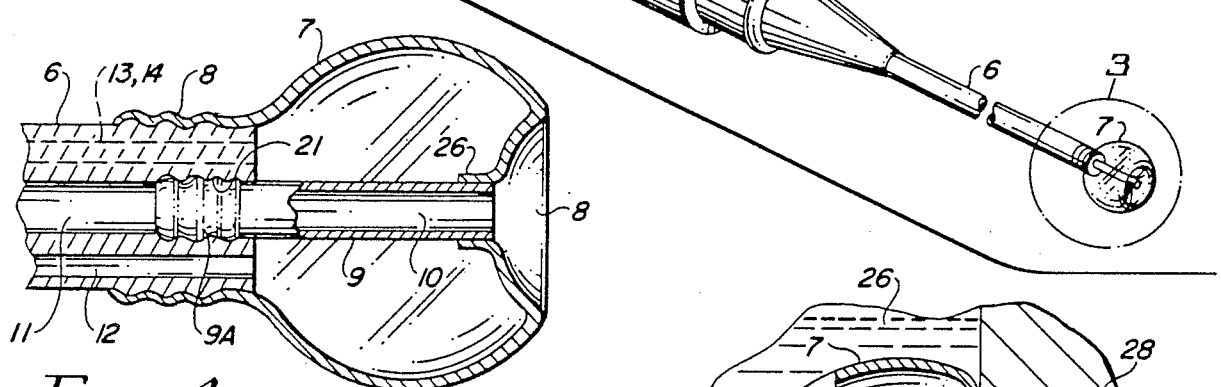
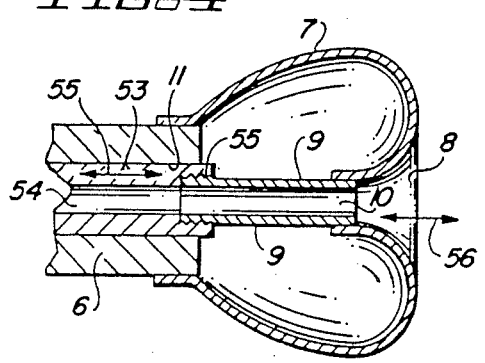
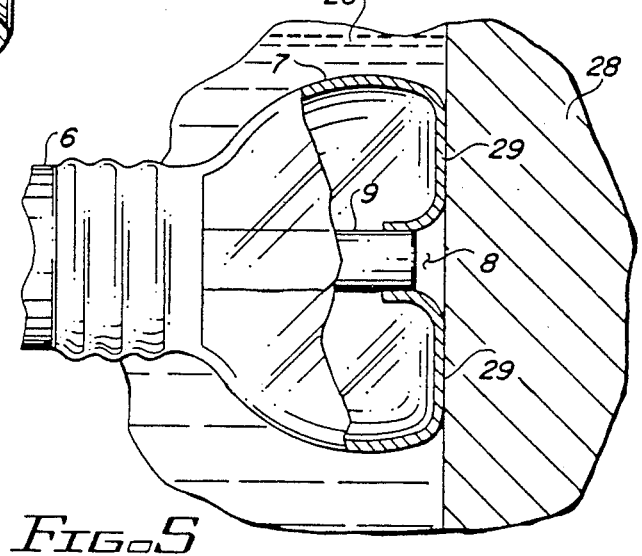

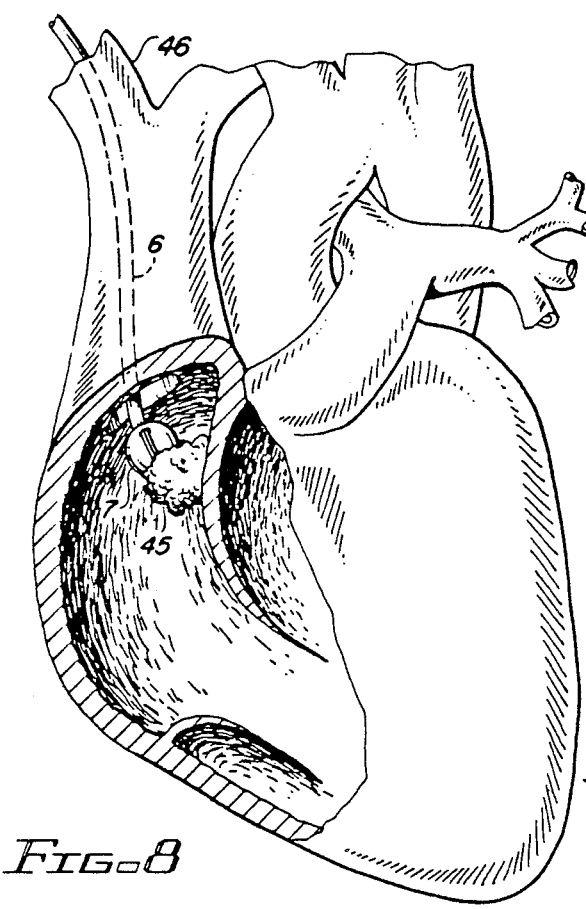
FIG-8
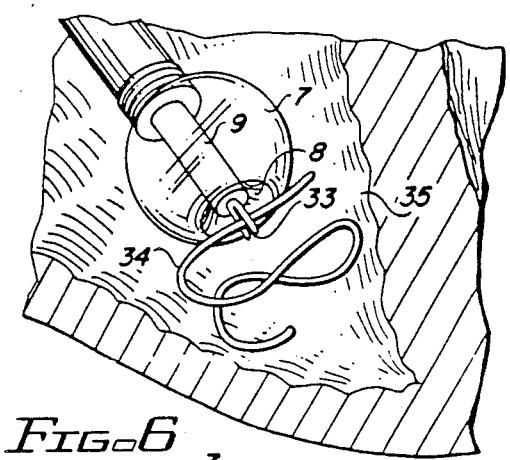
FIG-6
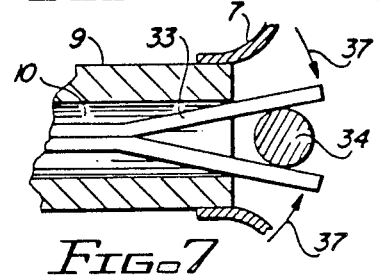
FIG-7
FIG-10
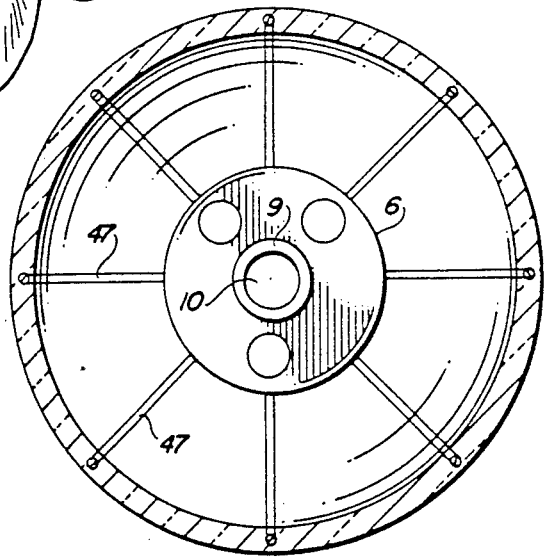
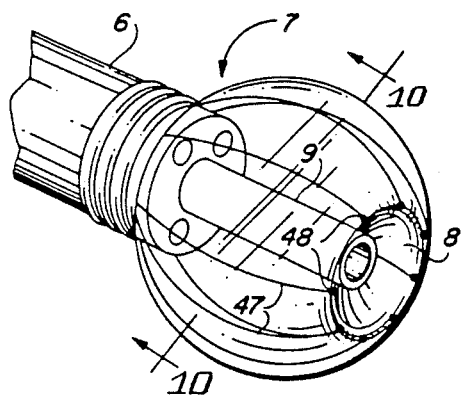
FIG-9
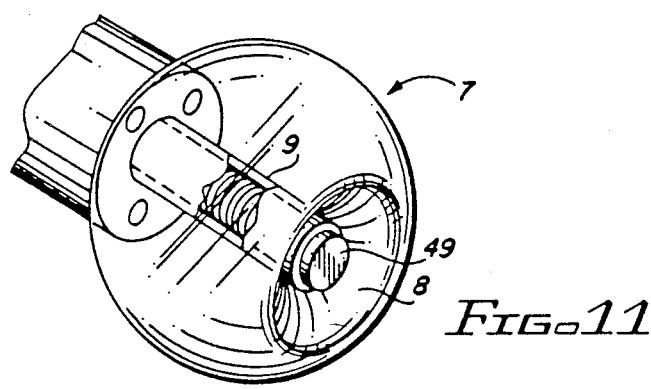
FIG-11

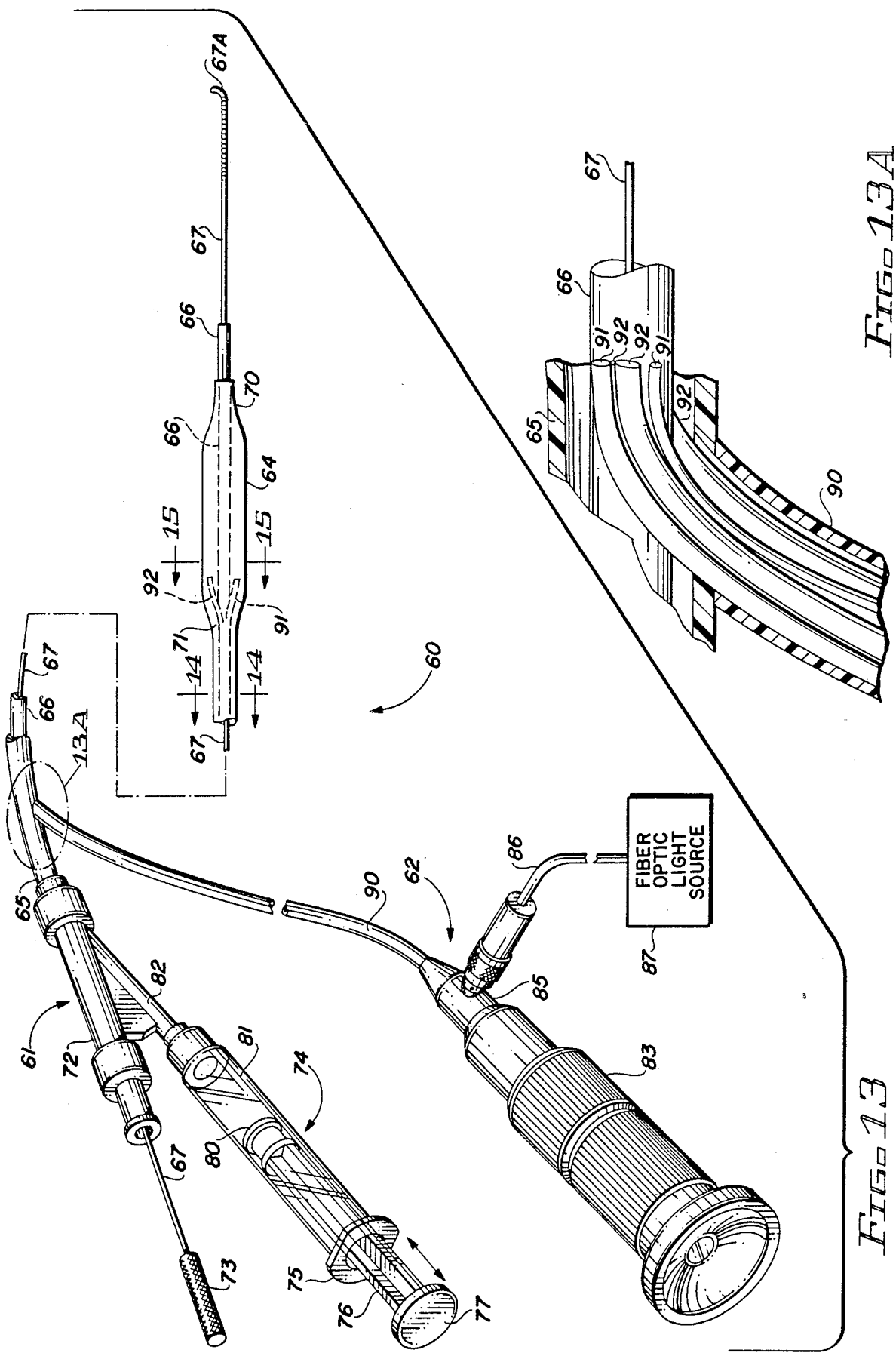

ANGIOPLASTY CATHETER WITH ILLUMINATION AND VISUALIZATION WITHIN ANGIOPLASTY BALLOON

CROSS-REFERENCE TO RELATED APPLICATION

This application is a continuation-in-part of my pending patent application "WORKING WELL BALLOON ANGISCOPE AND METHOD," Serial No. 008,276, filed on Jan. 28, 1987 patent no. 4,784,133 incorporated herein by reference.

BACKGROUND OF THE INVENTION

The invention relates to angioplasty catheters and associated procedures, and particularly to an improved means of illuminating and visualizing the interior of an artery and an obstruction therein before, during, and after an angioplasty procedure dilating the artery.

It is well known that buildup of lipid and calcium known as atherosclerotic plaque inside a coronary artery reduces the internal cross-sectional area of the vessel, leading to a reduction in blood flow to the heart muscle. Left untreated, the patient may progress to symptons of chest pain known as angina pectoris or progress to the stage of having a heart attack or myocardial infarction. In the majority of cases in patients with accelerated angina pectoris, or in the event of a myocardial infarction, the underlying mechanism appears to be blood clots or thrombus formation in the area of atherosclerotic plaque. In recent years, the technique of balloon angioplasty has been developed whereby a catheter with an elongated inflatable balloon thereon is passed to the narrowed arterial segment under guidance of an X-ray technique known as fluoroscopy. Contrast agents or "fluoroscopic dyes" are injected into the narrowed artery to aid passage of the catheter and to better delineate the narrowing. Once the balloon catheter is properly positioned, the balloon is inflated with saline solution and/or a contrast agent which then dilates the narrowing by compressing thrombus formation or by cracking and compressing plaque, which thereby serves to widen the lumen. Although this technique has revolutionized the treatment of both coronary and cardiac and peripheral vascular disease worldwide, there are some major problems associated with this technique. One problem is that the nature, configuration and degree of narrowing of the vessel is only approximately determined utilizing fluoroscopic techniques, even when multiple projections from different angles are obtained. Also, during and after the dilation procedure the success of the procedure can only be approximated with fluoroscopic techniques. It is important to monitor as closely as possible the dilation procedure, since the duration and success of the technique has direct bearing on the associated morbidity and mortality. Also, multiple fluoroscopic views are required before, during, and after the procedure, and add to the total duration of the procedure. Excessive amounts of contrast or dye agents thus may be required in producing these images and may pose a potential adverse affect to the other organs, such as the kidneys. Furthermore since it is well-known that the success of the angioplasty procedure depends on the type of obstruction (lipid alone, lipid with our without calcium and/or with or without associated thrombus), it would be highly desirable before beginning the dilation procedure to have accurate knowledge of the elements which constitute the obstruction. This information may be very desirable and may significantly affect physician-patient decisions.

Use of laser fibers extending into angioplasty catheter balloons to pass laser light through the wall of the balloon to disintegrate plaque in an artery also is known.

Fiber optic cardioscopes and angioscopes have been developed to allow visualization of intravascular or intracardiac structures without performing a major surgical procedure such as a thoracotomy to accomplish such visualization. In these devices, an inflatable transparent balloon is attached to the distal end of the fiber optic catheter. After the instrument is inserted into a blood vessel, the balloon is inflated and the instrument is advanced through the vein or artery to the desired location. The inflated balloon serves to displace blood, and when the lumen is occluded or the balloon comes in contact with the endothelium of a vessel or cardiac structure, direct viewing can be accomplished. Originally referred to as cardioscopes, fiber optic cardioscopes have become smaller in diameter and have come to be referred to as angioscopes to reflect their utility in intracardiac and intravascular viewing. More recently, angioscopy has been of use for diagnosis and therapy of systemic, coronary and pulmonary systems. One presently known flexible fiber optic angioscope design includes an inflatable end-balloon attached to the distal end of the fiberoptic angioscope. A hollow inflation channel, a light channel, and a viewing channel communicate with the interior of the balloon. Following insertion of the end balloon into a vessel, the balloon is inflated with air or liquid. The balloon serves to occlude a blood vessel or is abutted against an intracardiac structure or the like, and visualization is accomplished. Another design includes an inflatable balloon positioned near but not at the end of the angioscope and is referred to as a near-end-balloon angioscope. After passage of the near-end-balloon angioscope into a vessel, the balloon is inflated, which retards blood flow.

Thus, it is clear that there is an unmet need for an improved apparatus and technique for directly visualizing the interior of an artery and the configuration of an obstruction in the artery before, during, and after an angioplasty dilation procedure.

SUMMARY OF THE INVENTION

Accordingly, it is an object of the invention to provide an apparatus and method for effectuating direct visualization of an obstruction in a blood vessel or the like before, during, or after dilation thereof.

It is another object of the invention to provide an apparatus and method wherein the information obtained may significantly affect the morbidity and mortality of the procedure and may significantly affect physician-patient decisions.

It is another object of the invention to provide an angioplasty apparatus and method which increases the amount of information available concerning the condition of the obstruction in the artery before, during and after the procedure which may have a significant bearing on associated mortality and morbidity.

Briefly described, and in accordance with one embodiment thereof, the invention provides an angioplasty catheter including an elongated transparent balloon attached in fluid communication with an outer tube, a flexible inner catheter extending axially through the balloon end having a channel through which a flexible guide wire extends, and an annular channel between the inner catheter and the outer tube opening into the interior of a proximal end of the balloon, a distal end of the first channel opening into the balloon, an optical illumination fiber passing through the outer tube having a proximal end connected to a light source to produce light that emanates into the proximal end of the balloon and an optical visualizing fiber passing through the outer tube from the proximal interior portion of the balloon to an eyepiece. Illumination and visualization of both the interior of the artery and the configuration of an obstruction therein before, during and after dilation of the artery is thereby accomplished.

In another described embodiment of the invention, a "working well" recess is provided in the distal surface portion of a transparent balloon of an angioscope, the working well recess portion of the balloon including a centered opening into which the tube opens, so that the first channel provides a continuous, open path from a proximal end of the angioscope into the working well recess. After inserting a distal end of the flexible catheter into a vein or artery, the balloon is inflated, either with a gas or a transparent liquid, such as saline solution, and light conducted by the optical fiber through the second channel illuminates the region beyond the distal surface of the transparent balloon. In one described embodiment of the invention, the distal end portion of the inflated balloon is pressed against the wall of an intravascular structure, isolating the working well recess. Saline solution is forced through the first channel and the tube into the working well recess to flush out blood therein, allowing clear visualization (through the third channel) of the intravascular wall tissue bounding the working well recess. Various apparatus, such as a laser fiber, biopsy forceps, or tubular means for conducting sufficiently cold liquid to freeze the tissue or other substance adjacent to the working well recess, then may be passed through the first channel and the tube into the working well region. Ablation of the adjacent tissue or substance in the working well recess is thereby accomplished through the first channel and the tube while illumination is accomplished through the second channel and through the wall of the transparent balloon and accurate visualization is accomplished through the third channel and the wall of the transparent balloon. In another embodiment of the invention, accurate visualization of a procedure including retrieving a foreign object by means of a biopsy forceps is achieved.

BRIEF DESCRIPTION OF THE DRAWINGS

FIG. 1 is a partial perspective view of a prior art angioscope.

FIG. 2 is a partial perspective view of a complete angioscope in accordance with the present invention.

FIG. 3 is an enlarged partial perspective view of detail 3 of FIG. 2.

FIG. 4 is a section view along section line 4—4 of FIG. 3.

FIG. 5 is a partial cutaway section view useful in explaining the use of the angioscope of the present invention.

FIG. 6 is a partial perspective cutaway view illustrating utilization of the angioscope of the present invention to retrieve a foreign article.

FIG. 7 is a partial section view useful in explaining the procedure of FIG. 6.

FIG. 8 is a partial perspective cutaway view illustrating utilization of the angioscope of the present invention to perform a biopsy on an intracardiac tumor.

FIG. 9 is a partial perspective view of another embodiment of the angioscope of the present invention.

FIG. 10 is a section view along section line 10—10 of FIG. 9.

FIG. 11 is a partial perspective view of the angioscope in FIG. 3 illustrating introduction of a laser fiber into the working well cavity thereof.

FIG. 12 is a section view of an alternate embodiment of the angioscope of the present invention.

FIG. 13 is a diagram illustrating the angioplasty catheter/scope of the present invention.

FIG. 13A is an enlarged view of detail 13A of FIG. 13.

DESCRIPTION OF THE INVENTION

Figure 14:
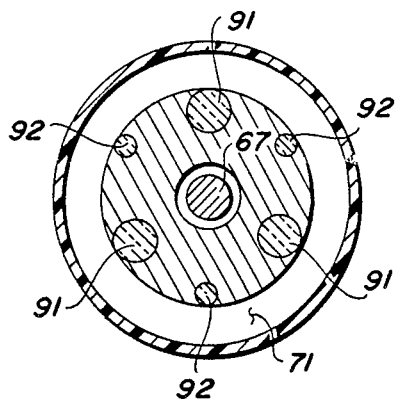
FIG. 14 is an enlarged section view taken along section line 14—14 of FIG. 13.

Referring now to FIG. 1, reference numeral 1 designates the end-balloon angioscope previously referred to. The inflatable clear plastic balloon 1B is attached by sutures or other means 2 to a flexible angioscope catheter 1A. Various channels are provided in catheter 1A. For example, an inflation port 3A, a viewing port 3B, and a light channel 3C are provided. This device perhaps represents the closest prior art to the present invention.

In accordance with the present invention, the distal end of a fiber optic angioscope of the present invention is shown in FIGS. 3 and 4. Catheter 6 represents the "flexible fiber optic extension" of the body 15 of angioscope 5. An eye piece 25 enables the physician to view a passage or cavity into which the distal end of angioscope 15 is introduced, and is attached to the proximal end of the body 15 of angioscope 5. An angulation know 16 controls the axial orientation of the distal tip of catheter 6 relative to body 15 of the angioscope. A laser fiber 23 or other instrument can be passed through a biopsy channel 11 of the catheter 6 to allow lasing, biopsy, or other procedure to be performed on tissue or other matter near or at the distal end of catheter 6. Such laser fiber or instrument can be introduced into the channel 11 before or after the catheter 6 is introduced into the vein, artery or other cavity. If this is done, after the catheter is introduced into the body, a clear chamber can be provided at the proximal end of the catheter, into which chamber blood can be drawn through which the instrument can be passed, to ensure that no air bubbles are forced by the instrument through channel 11 into the body.

Reference numeral 19 designates a source of transparent gas or liquid which is forced through tube 20 and channel 13 to inflate balloon 7. Air could be used as a gas, and saline solution could be utilized as a liquid. FIG. 11 shows the end 49 of a laser fiber 24.

In FIG. 2, light source 17 is connected by optical fiber 18 to angioscope 5 and extends through channel 12 of catheter 6 to provide illumination at the distal end of catheter 6. Channel 14 permits viewing of the region beyond the distal end of catheter 6.

In accordance with the present invention, inflatable balloon 7 is attached by sutures 8 or the like to the distal end of catheter 6. A recess 8, referred to herein as a "working well," has a central opening therein. The portion of balloon 7 forming that hole is attached by suitable bonding material to a rigid plastic sleeve 9 having passage 10 therethrough that opens into both working well 8 and central passage or "biopsy channel" 11 in catheter 6. The proximal end of tube 9 is threaded into a corresponding threaded area 21 at the distal portion of passage 11 in catheter 6.

In accordance with the present invention, flexible catheter 6 can be introduced in a conventional fashion through an intravascular path, into an intravascular structure or cavity. The balloon is inflated after the distal end of catheter 6 has been introduced into the intravascular structure or cavity. In FIG. 5, reference numeral 26 represents the interior of (for example) a chamber of the heart. Reference numeral 28 designates the endocardium. The distal end of working well balloon 7 is pressed against the surface of endocardium 28, deforming and/or flattening the balloon, as indicated by reference numerals 29. The flattening of the distal end balloon portion surrounding the working well 8 serves to displace blood from the adjacent lining or endocardium of the heart 26 and also serves to isolate the working well are 8 from the surrounding blood pool. Saline or other solution then can be delivered through channel 11 to flush the remaining blood from the working well region 8, making it possible for the physician to easily view the surface of endocardium 28 through catheter 6 and clear plastic balloon 7.

My initial experiments were performed using a working well balloon 7 formed of transparent polyurethane material which was formed by dipping a preshaped glass rod and ball into polyurethane, withdrawing it, and allowing the polyurethane to dry thereon. The glass then was broken free and cleared from the polyurethane. A small opening was made in the recessed working well 87 and a rubber sleeve 9 was secured thereto. The polyurethane balloon was attached to the end of a 4 millimeter Olympus flexible pediatric bronchoscope. A quartz fiber with its sheath was then passed through a one-way valve into and through the biopsy channel 11 of the bronchoscope and through the rubber sleeve 9 into the working well 8.

This device was used in my laser atrial septostomy experiments on two mongrel dogs. An internal jugular vein was used to gain vascular access. An incision large enough to accommodate the working well balloon angioscope catheter 6 was made into the vein wall, and the distal end of the angioscope 5 was inserted. The catheter 6 then was advanced to the superior vena cava and the balloon was inflated to a volume of approximately 2 cubic centimeters. The catheter 6 then was advanced to the interatrial septum, which then was visualized through the viewing port 14 and the distal transparent working well wall of balloon 7.

Nd:YAG laser light at a 40 watt level was delivered over a 2-3 second interval to the atrial septum via the quartz laser fiber. Although difficulties were encountered, including a failure of the material in the working well 8 and collapsing the balloon 7, which precluded further visualization, laser charring of the visualized tissue was observed during delivery of laser energy. I expect that if cold saline solution had been used instead of air to cool the quartz fiber during the delivery of the laser energy, the above problem would have been avoided Saline cooled quartz fiber systems are commercially available, and implementation thereof in the angioscope 5 should present no great difficulty. Another problem observed was that the polyurethane did not collapse satisfactorily because rather sharp edges were created where the polyurethane collapsed on itself. Transparent latex or other material may be more suitable.

Despite the problems encountered in the initial experiments, atrial septoscopy by means of laser energy using an optic angioscope described above appears to be practical and advantageous to existing methods of atrial septostomy.

Other potential applications of the working well balloon angioscope of the present invention include identification of intravascular or intracardiac foreign bodies which require extraction. FIGS. 6 and 7 illustrate this application, wherein a pair of biopsy forceps 33 or the like are introduced beyond the working well 8 of the balloon 7, which allows accurate visualization of the foreign object 34. (Object 34 might be a broken off portion of an endocardial pacemaker lead, catheter, or other object.)

Another potential application of the working well balloon angioscope is the direct visualization of biopsy sites of the myocardium or of a cardiac tumor. FIG. 8 illustrates this application, wherein a cardiac tumor 45 of heart 44 is being visualized via catheter 6 and working well balloon 7. Biopsy forceps such as 33 in FIGS. 6 and 7 could be utilized to remove a piece of tissue from the visualized site.

Another possible application of the working well balloon angioscope is in studies of cardiac arrythmias, wherein a number of thin flexible conductors 47 are embedded in the walls of the balloon 7, as shown in FIG. 9. These conductors 47 pass through a cable in the catheter 6 and terminate upon conductive electrodes 48 located on the outer balloon surface around the perimeter of working well 8, as shown in FIGS. 8 and 10. The electrodes 48 could be utilized to map the endocardium and ascertain the anatomic sites of micro-reentrant and/or ectopic foci. Direct correlation between observed tissue configuration and rhythm disturbance could thereby be achieved. After identification of the arrythmogenic foci, ablation or potential destruction by freezing or heating or by means of electrical, mechanical, chemical or laser energy could be accomplished. As another alternative, some of the electrodes such as 48 in FIG. 9 could be positioned on various other portions of the balloon than on its left or distal end portion. This may be advantageous for recording and mapping of electrical activity within the heart. The electrodes need not actually touch the endocardium, as the electrical signals in the endocardium are transmitted through the blood.

The above-described working well balloon angioscope also may have application in the study of the arrythmogenic and antiarrythmogenic substances, which could be instilled or injected through the biopsy channel 11 into the working well region 8 after the distal end of the balloon is abutted against the endocardium, thereby isolating the area which would be contacted by the arrythmogenic or antiarrythmogenic substances. Direct visualization of the site under study can confirm that the working well area has not moved from the intended site being studied.

Other potential applications of the working well balloon angioscope in conjunction with use of laser fibers introduced through the biopsy channel 11 include ablation of accessory (i.e., anomalous) pathways, the atrioventricular node, the His bundle, ectopic foci, hypertrophic (i.e., too thick) myocardium, mural thrombi (i.e., intracardiac clots), myxomas (tumors) and treatment of calcified, noncalcified, and congenital valvular stenosis.

An alternate embodiment of the invention is shown in FIG. 12, wherein the threaded left-hand end of the rigid tube 9 is threaded into a threaded hole 55 at the end of a passage 54 through an inner catheter 53 that is slidable within the central channel 11 of outer catheter 6. (The other channels 12, 13, and 14 shown in FIG. 3 also are included in the outer catheter 6 or the inner catheter 53, depending upon the amount of room available and other considerations.) The embodiment of the invention shown in FIG. 12 allows the inner catheter 53 to be moved relative to the outer catheter 6 in the direction of arrows 56. This provides the user with control over the depth of the working well 8, which in some cases might be advantageous.

Referring to FIG. 13, angioplasty catheter/scope 60 of the present invention includes a section 61 that consists of the control portion of a conventional angioplasty catheter. Angioplasty catheter/angioscope 60 also includes a proximal portion 62 of a conventional angioscope, and a catheter/balloon portion 63 of a conventional angioscope. In accordance with the present invention, a conventional angioscope has been modified by providing optic fibers from fiber optic source 87 extending through tube 90 through the outer sheath 65 and terminating in the proximal or left-hand portion of an elongated, inflatable, transparent balloon 64. The conventional angioscope also has been modified by other optical fibers 91 that extend from the proximal portion of the interior of inflatable balloon 64 through most of the length of outer sheath 65 then diverge into tube 90 and terminate in the eyepiece 83.

Control assembly 61 includes a hollow cylinder 72 from which outer sheath 65 extends. A semi-rigid, flexible inner catheter 66 extends through the length of outer sheath 65, axially through inflatable balloon 64, beyond the distal end of balloon 64. The distal or right-hand of balloon 64 is sealed to the outer surface of inner catheter 66, as indicated by reference numeral 70. A conventional guide wire 67 having a flexible helically wound tip 67A extends through inner catheter 66, through cylinder 72, and is connected to a removable narrow handle 73 by means of which a physician initially advances guide wire 67 ahead of the inner catheter 66 and balloon 64 through an artery to the proximity of an obstruction.

Outer sheath 65 is continuous with balloon 64. An open passage 71 between the outer surface of inner catheter 66 and outer sheath 65 allows fluid to be pumped into balloon 64 to inflate it, and thereby dilate the narrowed passage. Seal 70 prevents the fluid, which usually contains a fluoroscopic contrast agent, from escaping, allowing pressure buildup and inflation of balloon 64 to accomplish the dilation.

Outer sheath 65 extends into cylinder 61 and then diverges into a passage 82 to a syringe pump 74 by means of which the inflating fluid are pumped through passage 71 into balloon 64. Syringe pump 74 includes a plunger 76 that can be moved in the directions indicated by the arrows. Numeral 81 designates the volume containing the pumped fluid within syringe pump 74. Numeral 80 designates a sealed piston that forces the fluid in volume 81 through passage 82 and annular passage 71 into balloon 64. Numeral 75 designates a flange for engaging the fingers of the physician as his thumb presses on plate 77 of plunger 76 to depress plunger 76.

Tube 90 contains the optical illumination fibers 91 and the optical visualization fibers 92 all of which extend from the proximal end of balloon 64 along inner catheter 66 and diverge from it into tube 90 and to fiber optic light source 87 or eyepiece 83.

Figure 14A:
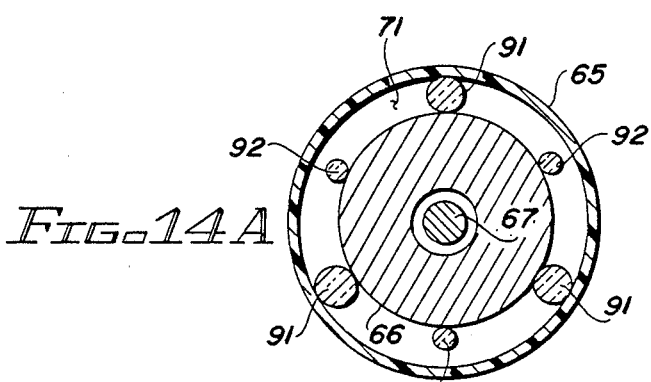
FIG. 14A is a section view of a modified embodiment of the invention.

As best seen in FIG. 14, optical illumination fibers 91 can be embedded in inner catheter 66. Optical illumination fibers 92 also can be embedded in inner catheter 66. Alternately, as shown in FIG. 14A, the optical visualization fibers 91 and the optical illumination fibers 92 can be attached along the outer surface of inner catheter 66, or can be disposed freely in the space 71 between the outer sheath 65 and the inner catheter 66.

Figure 15:
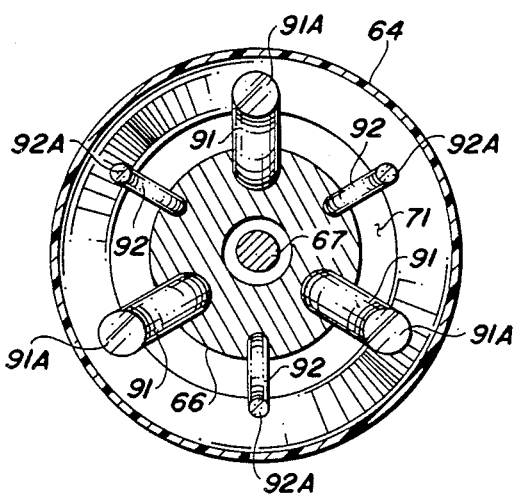
FIG. 15 is an enlarged section view taken along section line 15—15 of FIG. 13.

FIG. 15, taken along section line 15—15 of FIG. 13, shows how the distal ends of the optical fibers 91 and 92 diverge slightly from the inner catheter 66 to provide illumination and viewing of the interior of the balloon and the adjacent interior walls of the artery and the configuration of an obstruction by providing illumination in viewing along the direction of the inner catheter 66. Numerals 91A and 92A show the ends of the diverged fibers 91 and 92, respectively. Suitable lens are, of course, disposed in the ends of the visualization fibers.

Figure 16:
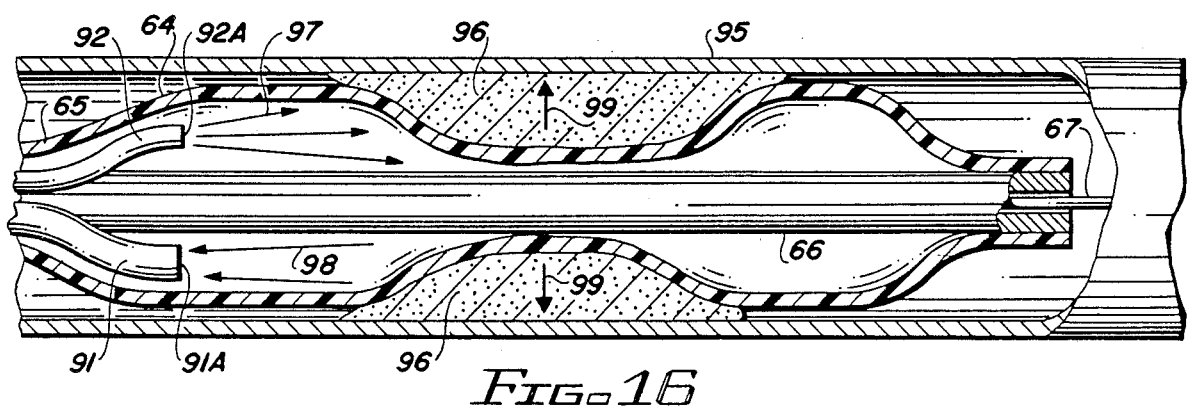
FIG. 16 is a section view diagram useful in illustrating the utilization of the angioplasty catheter/scope of FIG. 13.

FIG. 16 shows the balloon 64 positioned in an artery 95 after the balloon has been advanced and part way through a plaque obstruction 96. Arrows 97 illustrate light emanating from the end 92A of optical illumination fiber 92. The orientation of the ends 92A provides thorough illumination of the inner wall of artery 95 and the nature, degree, and configuration of the plaque obstruction 96. Reflection of light from the illuminated surfaces is indicated by arrows 98. The distal ends 91A of the optical visualization fibers 91 are oriented so that the entire illuminated region is visualized.

I believe that the above-described apparatus and technique will prove to be very practical. The optical fibers 91 and 92 can be extended through the interior of the outer sheath 65 without unduly increasing the diameter thereof. The fibers can be oriented so that three illumination fibers and three visualization fibers provide excellent illumination and visualization of the nature, degree, and configuration of the obstruction, enabling a physician to judge the desirability of postponing a dilation based on these variables. The technique also enables the physician to judge the progress of the dilation in the direction of arrows 99 as the balloon 64 is inflated. The physician also can judge much more accurately than has been previously possible the likelihood of the short and long term success of the dilation. The duration of the procedure can be shortened by reducing the number of fluoroscopic views needed. The amount of fluoroscopic contrast agent required can be kept at a minimum, reduCing the danger of complications because of deleterious effects of the fluoroscopic agent on other organs.

The diameter of the sheath 65 can be as small as approximately 1.5 to 5 millimeters, since the optic illumination fibers 92 can be as small as 0.3 millimeters in diameter, and the optic visualization fibers 91 can be as small as 0.5 millimeters in diameter, and the outside diameter of inner catheter 66 can be as small as 0.5 millimeters in diameter.

Direct visualization by means of the angioplasty catheter/scope as discussed may provide a new dimension to present angioplasty techniques, making it possible to minimize time under fluoroscopy.

While the invention has been described with respect to a number of embodiments, those skilled in the art will be able to make various modifications to the described embodiments without departing from the true spirit and scope of the invention. It is intended that all structures and techniques which are equivalent to those described herein in that they perform substantially the same function in substantially the same way to achieve the same results are to be considered to be within the scope of the invention. For example, the visualization fibers can be made to be axially slidable in the tubes 90 and 65 to allow better visualization, if necessary. The balloon may be inflated with gas instead of liquid.

I claim

1. Angioplasty apparatus comprising in combination:
   (a) an elongated, flexible, transparent balloon having a proximal end with a first opening therein and a distal end with a second opening therein;
   (b) an outer tube having a proximal end, and a distal end connected in sealed relationship to the proximal end of the balloon so that the first opening opens into the outer tube;
   (c) a flexible, semi-rigid inner catheter having a proximal end and a distal end, the inner catheter extending through the outer tube, into the first opening of the balloon, and out of the second opening of the balloon, a portion of the distal end of the balloon around the second opening being attached in sealed relationship to an outer surface of the inner catheter;
   (d) means for pumping fluid through a passage between the outer tube and the inner catheter to inflate the balloon;
   (e) means extending through the outer tube into the proximal end of the balloon for illuminating material on site, adjacent to the balloon, the illuminating means including an optical fiber having a distal end portion inside the balloon of the proximal end thereof, a midportion extending through the first opening and the outer tube, and a proximal end portion diverging from the outer tube and connected to a light source; and
   (f) means extending through the outer tube into the proximal end of the balloon for visualizing the illuminated material, the visualizing means including optical fiber means having a distal end portion generally symmetrically arranged around the inner catheter to allow visualization of a 360 degree band of an inner surface of a blood vessel artery and having a proximal end portion connected to an eyepiece, a midportion extending through the outer tube and the first opening just into the proximal end of the balloon, and a distal end portion overted to view the interior of the artery and the obstruction;

whereby a physician can generally symmetrically visualize the condition of the interior of the artery and the configuration of an obstruction therein before and/or during and/or after dilating the artery by inflating the balloon despite the presence of the inner catheter.

2. The angioplasty apparatus of claim 1 wherein the visualizing means includes a plurality of the optical fiber symmetrically disposed about the inner catheter, and the illuminating means includes a plurality of the optical fibers symmetrically disposed about the inner catheter.

3. The angioplasty apparatus of claim 1 wherein the optical fibers are attached to the inner catheter.

4. The angioplasty apparatus of claim 1 wherein the optical fibers are embedded in the wall of the inner catheter.

5. The angioplasty apparatus of claim 1 wherein each of the optical fibers of the visualizing means includes a lens in its distal end portion.

6. The angioplasty apparatus of claim 1 wherein the diameter of the balloon when inflated is in the range from about 1.5 to 3.0 millimeters.

7. The angioplasty apparatus of claim 6 wherein the diameter of the outer tube is in the range from about 1.5 to 2 millimeters.

8. The angioplasty apparatus of claim 1 including a guide wire extending through the inner catheter.

9. A method of using an angioplasty catheter including an elongated, flexible, transparent balloon having a proximal end with a first opening and a distal end with a second end, an outer tube having a distal end attached in sealed relationship to the proximal end of the balloon around the first opening, and a flexible, semi-rigid inner catheter extending through the outer tube and the first and second openings of the balloon and attached in sealed relationship to the distal end of the balloon around the second opening, the method comprising the steps of:
   (a) advancing a guide wire through a blood vessel to a site in the blood vessel;
   (b) advancing the inner catheter, outer tube, and balloon over the guide wire, to advance the balloon to the desired site;
   (c) illuminating a circumferential portion of the blood vessel at the site, including illuminating an obstruction at the site, by transmitting light from a light source through the outer tube and the first opening into the proximal end of the balloon; and
   (d) transmitting light reflected from the illuminated circumferential portion generally symmetrically around the inner catheter, through the first opening between the inner catheter and the outer tube into an eyepiece, thereby allowing a physician to visualize the entire circumferential portion of the vessel and also the obstruction at the site despite the presence of the inner catheter.

10. The method of claim 9 including forcing fluid through a space between the inner catheter and the outer tue into the balloon to inflate the balloon and thereby dilate the vessel, while visualizing the site and the condition of an inner wall of the vessel and the obstruction at the site.

11. The method of claim 10 wherein step (c) includes transmitting the light from the light source through a first optical fiber passing along the inner catheter in the outer tube and terminating in the balloon just past the proximal end thereof.

12. The method of claim 11 wherein step (d) includes transmitting the light reflected from the illuminated site through a second optical fiber to the eyepiece.

13. An endoscope comprising in combination:
   (a) an inflatable transparent balloon;
   (b) a flexible catheter having first and second channels therein extending from a proximal end to a distal end thereof, the second channel opening into the interior of the balloon, a proximal portion of the balloon being sealed to a distal end of the flexible catheter;
   (c) tubular means for extending from the distal end of the flexible catheter through the balloon extending the first channel through the balloon so that the extended first channel opens into a region beyond a distal portion of the balloon, the distal portion of the balloon being sealed to a distal end portion of the tubular means;

(d) means passing through the flexible catheter outside of the first channel for producing light that emanates from a distal end of the flexible catheter;

(e) means passing through the flexible catheter outside of the first channel for effectuating viewing of the region illuminated by the light producing means through the balloon; and (f) means passing through the first channel beyond the distal end portion of the tubular means for interacting with tissue or substance beyond the balloon illuminated by the light producing means and viewed through the viewing means.

* * * * *